(12) United States Patent
Smith

(10) Patent No.: US 11,918,749 B2
(45) Date of Patent: Mar. 5, 2024

(54) SINGLE USE SINGLE DOSE NITROUS OXIDE DELIVERY SYSTEM

(71) Applicant: Matthew Smith, Carson City, NV (US)

(72) Inventor: Matthew Smith, Carson City, NV (US)

(*) Notice: Subject to any disclaimer, the term of this patent is extended or adjusted under 35 U.S.C. 154(b) by 743 days.

(21) Appl. No.: 17/071,155

(22) Filed: Oct. 15, 2020

(65) Prior Publication Data

US 2022/0118211 A1    Apr. 21, 2022

(51) Int. Cl.
| | |
|---|---|
| *A61M 16/00* | (2006.01) |
| *A61M 16/06* | (2006.01) |
| *A61M 16/08* | (2006.01) |
| *A61M 16/12* | (2006.01) |
| *F17C 1/00* | (2006.01) |

(52) U.S. Cl.
CPC .......... *A61M 16/12* (2013.01); *A61M 16/009* (2013.01); *A61M 16/06* (2013.01); *A61M 16/0875* (2013.01); *F17C 1/00* (2013.01); *A61M 2202/0208* (2013.01); *A61M 2202/0283* (2013.01); *A61M 2209/082* (2013.01); *F17C 2201/0109* (2013.01); *F17C 2201/058* (2013.01); *F17C 2221/011* (2013.01); *F17C 2221/03* (2013.01); *F17C 2270/025* (2013.01)

(58) Field of Classification Search
CPC .... A61M 16/12; A61M 16/009; A61M 16/06; A61M 16/0875; A61M 2202/0208; A61M 2202/0283; A61M 2209/082; F17C 1/00; F17C 2201/0109; F17C 2201/058; F17C 2221/011; F17C 2221/03; F17C 2270/025
See application file for complete search history.

(56) References Cited

U.S. PATENT DOCUMENTS

| | | | | |
|---|---|---|---|---|
| 3,556,097 A | * | 1/1971 | Wallace | A61M 16/1065 55/510 |
| 5,986,240 A | * | 11/1999 | Schmitt | F17C 13/084 219/391 |
| 9,399,108 B2 | * | 7/2016 | Bird | A61M 16/12 |
| 2018/0149315 A1 | * | 5/2018 | Despres | H01L 21/67017 |
| 2019/0314595 A1 | * | 10/2019 | Dube | A61M 16/20 |

* cited by examiner

*Primary Examiner* — Steven O Douglas
(74) *Attorney, Agent, or Firm* — Mark A. Goodman

(57) ABSTRACT

An embodiment of a single use nitrous oxide solution delivery system can be used in a prehospital setting such as in ambulances. A container can be filled with a predetermined relative concentration of nitrous oxide and oxygen gases. The container is sized to be stored in a repository within an automated dispensing cabinet (ADC) for medications. The container is connected to a regulator which includes a main control dial configured to allow a health care provider to adjust the volumetric flow rate of the nitrous oxide and oxygen gas mixture used by a patient. A scavenger can be optionally connected to a patient's mask and configured to remove exhaled gas. Another embodiment of a single use nitrous oxide solution delivery system can be used within hospitals and other medical buildings.

6 Claims, 4 Drawing Sheets

SINGLE USE SINGLE DOSE NITROUS OXIDE DELIVERY SYSTEM

BACKGROUND OF THE INVENTION

1. Field of the Invention

The present invention relates generally to systems and methods for delivering nitrous oxide to patients. More particularly, the present invention relates to systems and methods for delivering a single dose of nitrous oxide from a single use container.

2. Description of Related Art

A current problem with nitrous oxide use in a large setting such as the emergency department of a hospital is that there is no way to monitor or control its use, and it has a high risk and potential for abuse. Currently, nitrous oxide is stored in large tanks which is acceptable in a small setting of a dentist office where there is constant supervision but is not acceptable in a larger setting of a hospital. When not in use, the tanks are usually stored in a supply closet. Many employees such as nurses, technicians, suppliers, and cleaning personnel all have access to the tanks, creating the potential for abuse. There is no adequate system to track and regulate the use of nitrous oxide. Often when nitrous oxide is needed in the hospital, the tanks are empty and there is no way to account for the use. Large jars of controlled substances like morphine are not stored in an unsecured closet. Likewise, a large tank of a controlled substance like nitrous oxide should not be stored in a closet.

Medications in the hospital are kept in locked medication delivery devices that have different names depending on the manufacturer, e.g. Pyxis, Omnicell, etc. Single doses of controlled medications are kept in these devices. When a nurse has an order for morphine from a prescribing provider, the nurse will then go to the Pyxis and check out a single dose of morphine. The nurse has to enter the count in the drawer before and after removing the vial. A count is performed of all the controlled substances in the machine by two nurses at the beginning and end of every shift. If the count does not add up, then they are able to look through the records to see which nurses have accessed that drawer throughout the day to account for the loss of a medication. There is a significant amount of research showing the benefits of having single use nitrous oxide in the emergency department, especially in the pediatric population. There is a need in the medical field for a single use delivery system for tracking the usage of nitrous oxide.

SUMMARY OF THE INVENTION

One embodiment of a single use nitrous oxide solution delivery system can be used in a prehospital setting such as in ambulances. A container can be filled with a predetermined relative concentration of nitrous oxide and oxygen gases. For example, the container can be filled with a mixture of 50% nitrous oxide and 50% oxygen. The container is preferably sized to be stored in a repository within an automated dispensing cabinet (ADC) for medications. The container is operatively connected to a regulator. The regulator includes a main control dial configured to allow a health care provider to adjust the volumetric flow rate of the nitrous oxide and oxygen gas mixture used by a patient. A scavenger can be optionally connected to a patient's mask and configured to remove exhaled gas.

Another embodiment of a single use nitrous oxide solution delivery system can be used within hospitals and other medical buildings. This system has a more complex regulator and a scavenger operatively connected to a mask worn by a patient. A container is filled with 100% nitrous oxide and is attached to a regulator. The regulator has an inlet oxygen port, an inlet nitrous oxide port, and an outlet gas mixture port. A scavenger includes tubing that connects to ventilation ports of the mask. The scavenger further includes a flutter valve covering the ventilation ports. The flutter valve is configured to open when the patient exhales, enabling exhaled gas to exit through a vacuum in a wall so that other people around the patient will not be exposed to the nitrous oxide.

These and other features and advantages will be apparent from reading of the following detailed description and review of the associated drawings. It is to be understood that both the forgoing general description and the following detailed description are explanatory and do not restrict aspects as claimed.

DETAILED DESCRIPTION OF THE INVENTION

The following descriptions relate principally to preferred embodiments while a few alternative embodiments may also be referenced on occasion, although it should be understood that many other alternative embodiments would also fall within the scope of the invention. The embodiments disclosed are not to be construed as describing limits to the invention, whereas the broader scope of the invention should instead be considered with reference to the claims, which may be now appended or may later be added or amended in this or related applications. Unless indicated otherwise, it is to be understood that terms used in these descriptions generally have the same meanings as those that would be understood by persons of ordinary skill in the art. It should also be understood that terms used are generally intended to have the ordinary meanings that would be understood within the context of the related art, and they generally should not be restricted to formal or ideal definitions, conceptually encompassing equivalents, unless and only to the extent that a particular context clearly requires otherwise. In light of the present disclosure, those of ordinary skill in the art should also appreciate that many changes can be made relative to the disclosed embodiments while still obtaining a comparable function or result without departing from the spirit and scope of the disclosure.

For purposes of these descriptions, a few wording simplifications should also be understood as universal, except to the extent otherwise clarified in a particular context either in the specification or in particular claims. The use of the term "or" should be understood as referring to alternatives, although it is generally used to mean "and/or" unless explicitly indicated to refer to alternatives only, or unless the alternatives are inherently mutually exclusive. Furthermore, unless explicitly dictated by the language, the term "and"

may be interpreted as "or" in some instances. When referencing values, the term "about" may be used to indicate an approximate value, generally one that could be read as being that value plus or minus half of the value. "A" or "an" and the like may mean one or more, unless clearly indicated otherwise. Such "one or more" meanings are most especially intended when references are made in conjunction with open-ended words such as "having," "comprising" or "including." Likewise, "another" object may mean at least a second object or more. Thus, in the context of this specification, the term "comprising" is used in an inclusive sense and thus should be understood as meaning "including, but not limited to." As used herein, the use of "may" or "may be" indicates that a modified term is appropriate, capable, or suitable for an indicated capacity, function, or usage, while considering that in some circumstances the modified term may sometimes not be appropriate, capable, or suitable.

Figure 1:
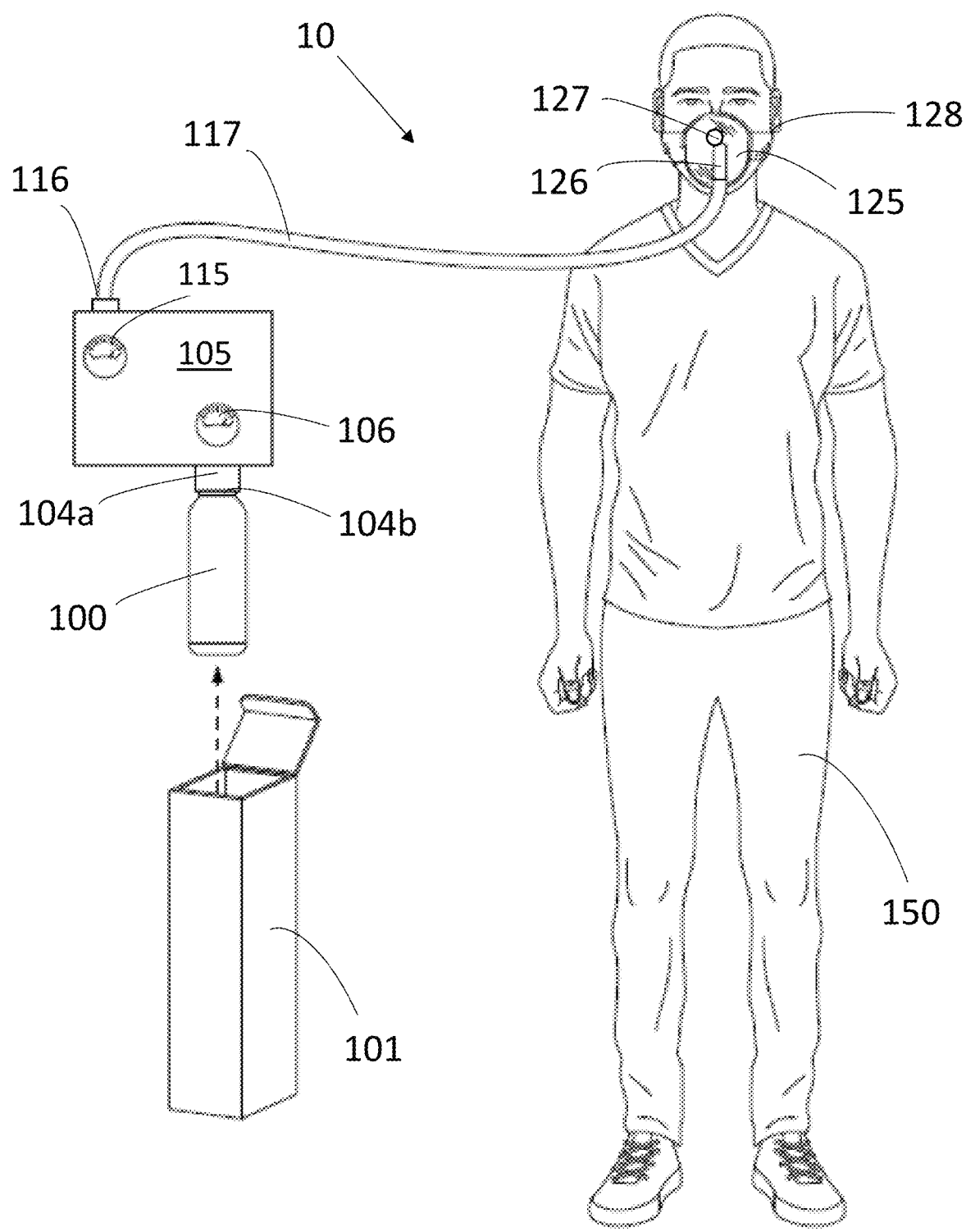
FIG. 1 illustrates an embodiment of a single use nitrous oxide solution delivery system.

FIG. 1 illustrates an embodiment of a single use nitrous oxide solution delivery system 10. The system 10 can be used in a prehospital setting such as in ambulances. Other medical uses can include military settings, where suction needed for a scavenger is not readily available. A container 100 is shown removed from a repository 101. The container 100 is filled with a predetermined relative concentration of nitrous oxide and oxygen gases. For example, the container 100 can be filled with a mixture of 50% nitrous oxide and 50% oxygen. An objective is for the system 10 to provide a flow of gas mixture to a patient for approximately ten minutes. The container 100 can be filled with various relative concentrations but the concentration of nitrous oxide cannot exceed 70%. The container 100 is preferably sized to fit and be stored in a rectanguloid repository 101 within an automated dispensing cabinet (ADC) for medications (i.e. automated medication dispensing cabinet system). Common ADC medication systems that can be utilized include Pyxis, Omnicell, Capsa, and the like. The repository 101 is preferably a rectanguloid sized to have a height no greater than eleven inches, a width no greater than five inches, and a depth no greater than eight inches. Preferably, the container 100 has a cylindrical shape. The container 100 preferably has a diameter no greater than five inches and a height no greater than eleven inches to enable it to fit inside a repository 101. An example container 100 has a diameter of three inches and a height of six inches.

The container 100 is operatively connected to a regulator 105. For example, the regulator can include an adaptor 104a with female threads. A container 100 with a male thread adaptor 104b can be screwed into the female threaded adaptor 104a. The regulator 105 is comprised of a durable material, preferably a metal. A pressure dial (gauge) 106 can measure the inlet pressure of the nitrous oxide gas. The pressure dial 106 can also be used to notify a health care provider that the nitrous oxide amount in the container 100 is running low. The regulator 105 further includes a main control dial 115 configured to adjust the volumetric flow rate of the nitrous oxide and oxygen gas mixture.

The main control dial 115 is operatively connected to an outlet tube tree 116. The outlet tube tree 116 can connect to a plurality (one or more) of tubes 117 transporting the gas mixture to a patient 150. Although the plurality of tubes 117 appears as one tube in FIG. 1, the plurality can include one or more tubes. The outlet tube tree 116 connects to a mask 125 worn by the patient 150. The mask 125 includes tubing 126 for connecting to the plurality of tubes 117 and for operatively connecting to the regulator 105. The mask 125 further includes ventilation ports 127 with pressure valves. The pressure valves are configured to open the ventilation ports 127 during exhalation, enabling exhaled gas to exit the ventilation ports 127. The pressure valves are further configured to close the ventilation ports 127 during inhalation. The mask 125 fits over a patient's head covering the mouth and nose using an elastic 128 and is preferably constructed of rubber.

Figure 2:
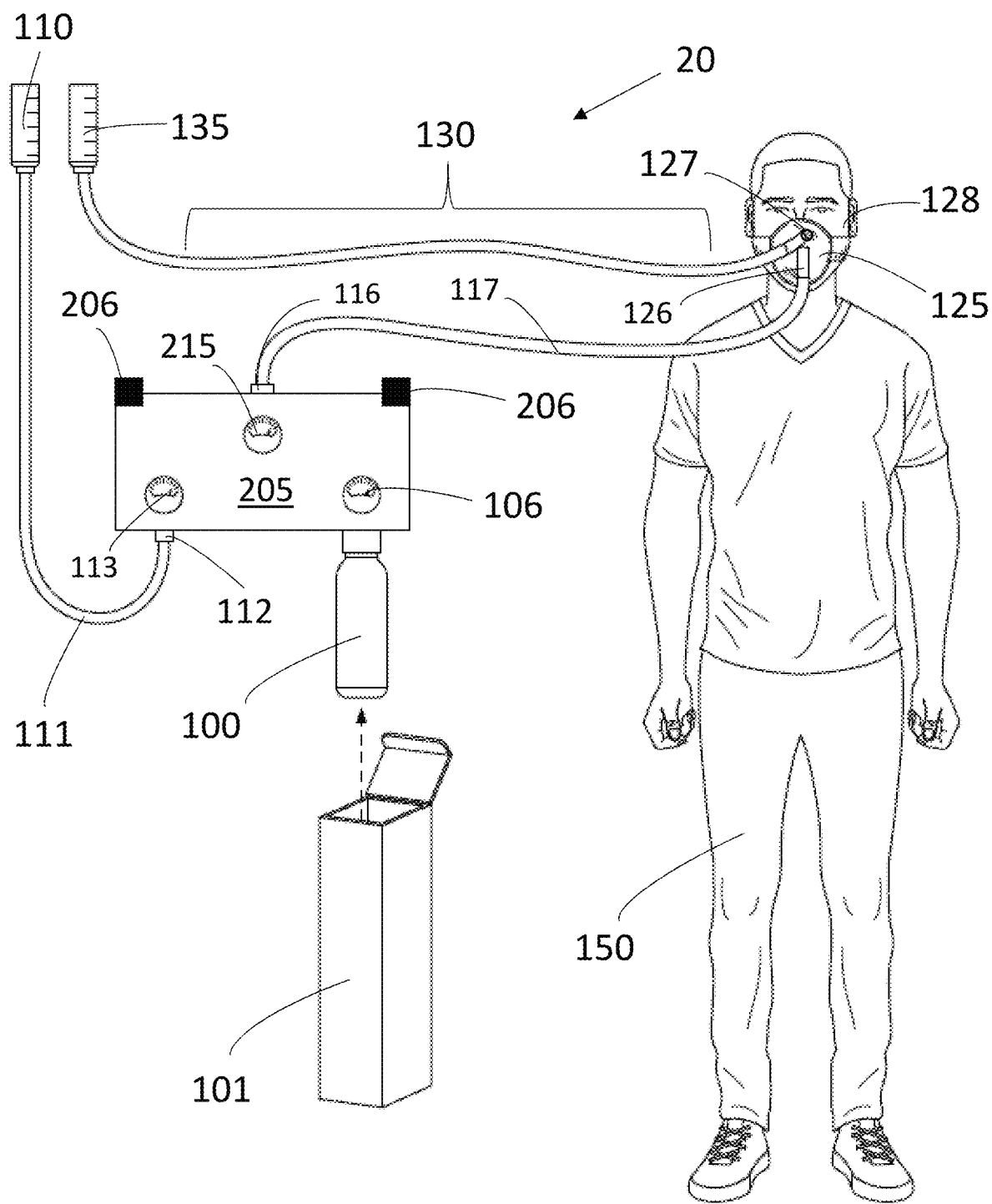
FIG. 2 illustrates a second embodiment of a single use nitrous oxide solution delivery system.

With cross reference to FIG. 2, a scavenger 130 is an optional component for system 10 that is unnecessary when the system 10 is used outdoors or in areas with adequate ventilation. In a situation where the system 10 is used indoors, a scavenger 130 can be attached to the mask 125. The scavenger 130 comprises tubing that connects to the ventilation ports 127 of the mask 125. The scavenger 130 can include a small Y-shaped piece of tubing. The scavenger 130 tubing is operatively connected to a vacuum 135, enabling the passage of exhaled gas (which includes nitrous oxide) away from an enclosed space around a patient 150.

FIG. 2 illustrates another embodiment of a single use nitrous oxide solution delivery system 20. Nitrous oxide delivery system 20 is similar to system 10 but has a more complex regulator 205 and a scavenger 130 operatively connected to a mask 125. Delivery system 20 is designed for use within hospitals and other medical buildings. A container 100 is filled with 100% nitrous oxide and is shown removed from a rectanguloid repository 101. The repository 101 is preferably a rectanguloid and sized to have a height no greater than eleven inches, a width no greater than five inches, and a depth no greater than eight inches. The repository 101 can hold a plurality of oxygen tubes 111 for operatively connecting the regulator 205 to an oxygen source 110. In addition to holding the container 100 and the oxygen tubes 111, the repository 101 can also hold a mask 125 and a scavenger 130. The container 100 is preferably sized to be stored in the repository 101 within an automated dispensing cabinet (ADC) for medications. Preferably, the container 100 has a cylindrical shape. The container 100 preferably has a diameter no greater than five inches and a height no greater than eleven inches to enable it to fit inside a repository 101. The container 100 is operatively connected to a regulator 205. At the top of the regulator 205, clips 206 can be employed to attach the regulator 205 to a patient's bed. For example, the regulator can include an adaptor 104a with female threads. A container 100 with a male thread adaptor 104b can be screwed into the female threaded adaptor 204a. The regulator 205 is comprised of a durable material, preferably a metal, and is more complex than the regulator 105 illustrated in FIG. 1. The regulator 205 has a rectangular shape although other shapes can be implemented. A pressure dial (gauge) 106 can measure the inlet pressure of the nitrous oxide gas and a valve can control the volumetric flow to regulate the inlet pressure. The pressure dial 106 can also be used to notify a health care provider that the nitrous oxide amount in the container 100 is running low. The regulator 205 is operatively connected to an oxygen source 110. The oxygen source 110 can connect to a plurality (one or more) of oxygen tubes 111. The plurality of oxygen tubes 111 can attach to an oxygen tube tree 112 attached to the regulator 205. The tube tree 112 is preferably constructed of metal or a similar durable material. Another pressure dial 113 can measure the inlet pressure of the oxygen gas and a valve can control the volumetric flow to regulate the inlet pressure. Thus, the regulator 205 can control the volumetric flow of a mixture of nitrous oxide and oxygen gases.

The regulator 205 further includes a main control dial 215 configured to adjust the concentration of the mixture of oxygen and nitrous oxide gas. The regulator 205 is configured to mix the inlet 100% nitrous oxide with the inlet 100% oxygen to a predetermined relative concentration. Using the main control dial 215, a health care provider can turn the gas on or off and adjust the gas mixture to a predetermined relative concentration. For safety reasons, the main control dial 215 is configured to not allow a concentration of greater than 70% nitrous oxide. The concentration settings on the main control dial 215 can range from 0% nitrous oxide (100% oxygen) to a maximum of 70% nitrous oxide (30% oxygen). For example, the dial 215 can have settings for nitrous oxide to oxygen ratios of 70:30, 60:40, 50:50, 40:60, 30:70, 20:80, 10:90, and 0:100. Further, a safety valve can be installed in the regulator 205 to prevent the system 10 from operating without an oxygen source 110. For example, if the oxygen inlet pressure dropped to zero the safety valve would shut down the regulator 205 to prevent the patient receiving a dosage of 100% nitrous oxide. The main control dial 215 can also include a gauge to measure the outlet gas mixture pressure.

The main control dial 215 is operatively connected to an outlet tube tree 116. The outlet tube tree 116 can connect to a plurality of tubes 117 transporting a gas mixture to a patient 150. The outlet tube tree 116 connects to a mask 125 worn by the patient 150. The mask 125 is preferably a simple disposable oxygen mask with some modifications. The mask 125 includes tubing 126 for connecting to the plurality of tubes 117 and for operatively connecting to the regulator 105. The mask 125 further includes ventilation ports 127 with pressure valves. The pressure valves are configured to open the ventilation ports 127 during exhalation, enabling exhaled air to exit the ventilation ports 127. The pressure valves are further configured to close the ventilation ports 127 during inhalation. The mask 125 fits over a patient's head covering the mouth and nose using an elastic 128 and is preferably constructed of rubber.

The scavenger 130 includes tubing that connects to the ventilation ports 127 of the mask 125. The scavenger further includes a flutter valve covering the ventilation ports 127. The flutter valve is configured to open when the patient 150 exhales, enabling exhaled gas to exit through a vacuum 135 in a wall so that other people around the patient 150 will not be exposed to the nitrous oxide.

Once the single use delivery system 20 has been completed, the mask 125, scavenger 130, and tubing can be discarded as normal for single use medical devices. The nitrous oxide container 100 can be recycled and returned to a manufacturer for refilling. The regulator 205 can be sanitized and stored for later use by another patient, so that another repository 101 holding the nitrous oxide container 100 and other products can be checked out of an ADC medication system.

Figure 3:
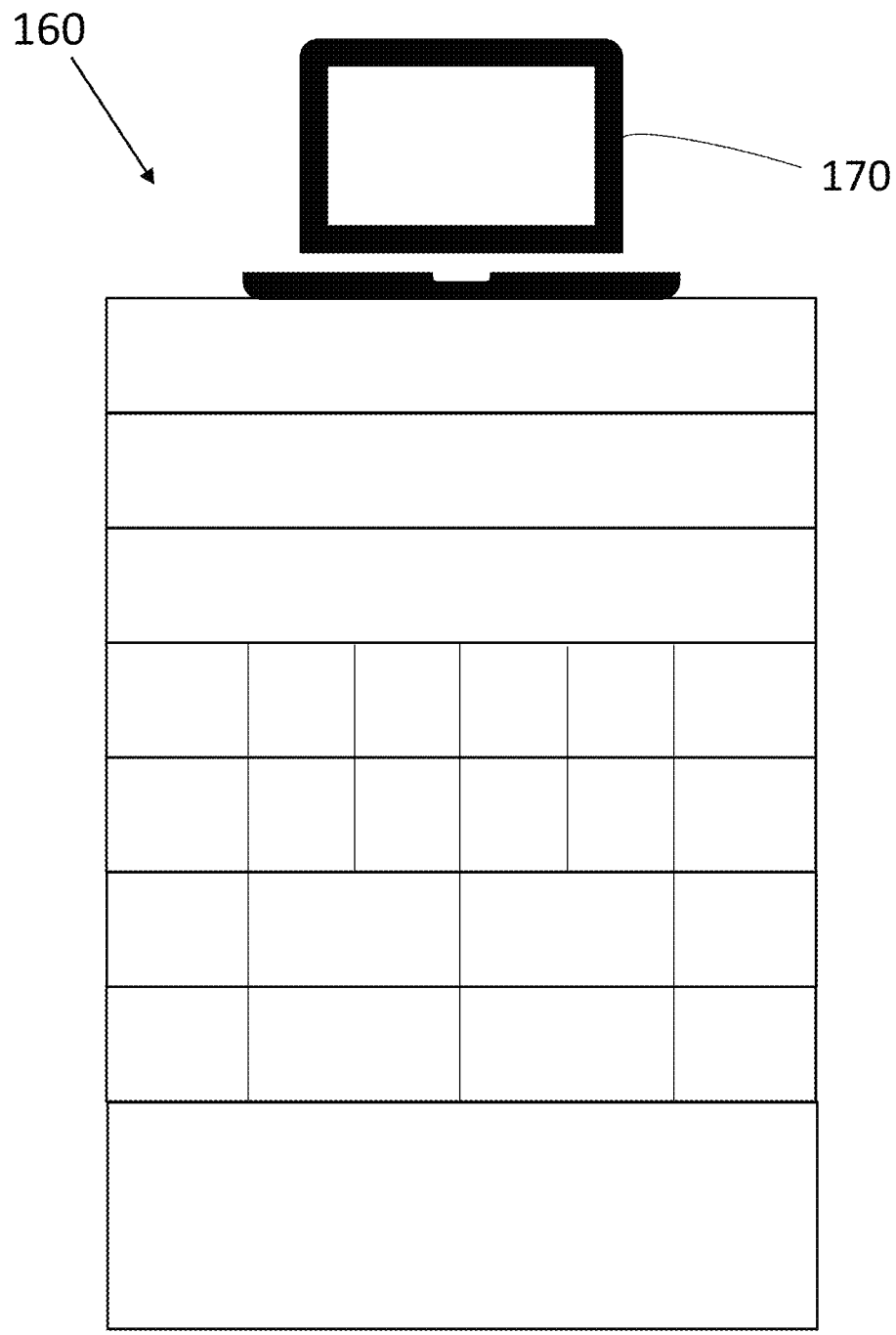
FIG. 3 illustrates an example ADC medication system.

FIG. 3 illustrates an example ADC medication system 160. The ADC medication system 160 can be a Pyxis, Omnicell, Capsa, and the like. The ADC medication system 160 resembles a cabinet with drawers. A computer 170 is shown implemented in the ADC medication system 160.

Figure 4:
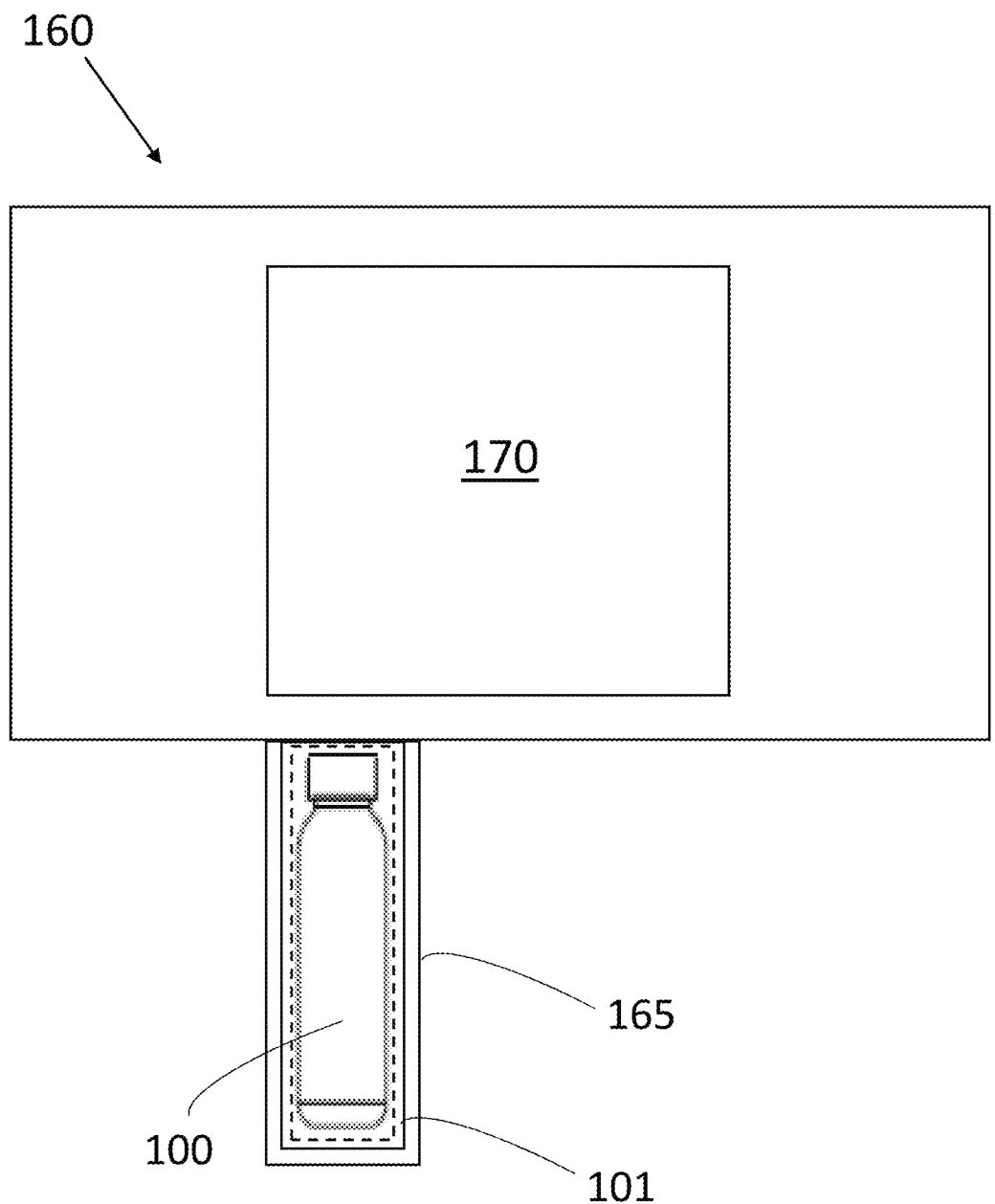
FIG. 4 illustrates a single use nitrous oxide container in an ADC medication system.

FIG. 4 illustrates a single use nitrous oxide container 100 in an ADC medication system 160. A drawer 165 is shown in an open position with a repository 101 holding a nitrous oxide container 100. The nitrous oxide container 100 is surrounded by broken lines to indicate that the container 100 is enclosed within the rectangular shaped repository 101.

What is claimed is:
1. A cylindrical single use nitrous oxide solution delivery system, the system comprising:
 a. a container having:
  a height no greater than eleven inches;
  diameter no greater than five inches;
  thereby allowing the container to fit into a repository of an automated medication dispensing cabinet system;
 b. wherein the container is filled with 100% nitrous oxide;
 c. a regulator operatively connected to the container;
 d. the regulator is further operatively connected to a source of 100% oxygen;
 e. the regulator is configured to mix the 100% nitrous oxide with the 100% oxygen to a predetermined relative concentration;
 f. the regulator is configured to control volumetric flow of the mixture;
 g. a mask comprising ventilation ports with pressure valves;
 h. the pressure valves configured to open the ventilation ports during exhalation, enabling exhaled air to exit the ventilation ports;
 i. the pressure valves further configured to close the ventilation ports during inhalation;
 j. the mask configured to cover the mouth and nose of a patient; and
 k. a plurality of oxygen tubes operatively connected to the mask.

2. The system of claim 1, wherein the predetermined relative concentration of nitrous oxide and oxygen falls in the range of: 0% nitrous oxide and 100% oxygen to 70% nitrous oxide to 30% oxygen.

3. The system of claim 1, wherein the predetermined relative concentration of nitrous oxide to oxygen ratio is 50% nitrous oxide to 50% oxygen.

4. The system of claim 1 further comprising a scavenger operatively connected to the mask, the scavenger comprising:
 a. tubing operatively connected to the ventilation ports of the mask; and
 b. the tubing is operatively connected to a vacuum, enabling the passage of exhaled gas away from an enclosed space around the patient.

5. The system of claim 1, further comprising a safety valve configured to prevent the delivery of 100% nitrous oxide.

6. A single use nitrous oxide delivery system, the system comprising:
 a. a box comprising:
  i. a plurality of oxygen tubes;
  ii. the plurality of oxygen tubes configured to attach to an oxygen supply in a room;
  iii. wherein the plurality of oxygen tubes is further configured to attach to a regulator;
  iv. a mask comprising ventilation ports and a rubber elastic able to fit over a patient's head covering the mouth and nose;
  v. wherein the mask further comprises tubing for operatively connecting the mask to the regulator;
  vi. a scavenger operatively connected to the mask; and
  vii. a container for storing compressed gas;
 b. the scavenger comprising:
  i. tubing operatively connected to the ventilation ports of the mask;
  ii. the tubing is further operatively connected to a vacuum in a wall;
  iii. a flutter valve covering the ventilation ports; and
  iv. the flutter valve configured to open during exhalation, enabling exhaled gas to exit through the vacuum; and
  v. the flutter valve further configured to close during inhalation;

c. the container being sized to fit into a rectanguloid repository of an automated medication dispensing cabinet system, the repository having:
   i. a height no greater than eleven inches;
   ii. a width no greater than five inches;
   iii. a depth no greater than eight inches;
   iv. a male threaded adaptor; and
   v. a mixture of compressed nitrous oxide and compressed oxygen;
   vi. a regulator operatively connected to the container, the regulator comprising:
   i. a durable structure with a plurality of ports;
   ii. a first tube tree comprising a plurality of oxygen tubes operatively connected to the regulator;
   iii. a first pressure dial operatively connected to the first tube tree;
   iv. the first pressure dial measuring oxygen pressure;
   v. a female threaded adaptor enabling the connection of the container;
   vi. a second pressure dial operatively connected to the container;
   vii. the second pressure dial measuring nitrous oxide pressure;
   viii. a second tube tree comprising a plurality of tubes operatively connected to the regulator;
   ix. a main control dial operatively connected to the second tube tree;
   x. the main control dial configured to adjust the concentration of the mixture;
   xi. wherein the main control dial is further configured to not allow a concentration of greater than 70% compressed nitrous oxide; and
   xii. clips affixed to the regulator enabling the regulator to be attached to a side rail of a patient's bed.

\* \* \* \* \*